US009968233B2

United States Patent
Strang

(10) Patent No.: US 9,968,233 B2
(45) Date of Patent: May 15, 2018

(54) AUTOMATICALLY DRIVEN CLEANING DEVICE

(71) Applicant: Vorwerk & Co. Interholding GmbH, Wuppertal (DE)

(72) Inventor: Benjamin Strang, Solingen (DE)

(73) Assignee: Vorwerk & Co. Interholding GmbH, Wuppertal (DE)

( * ) Notice: Subject to any disclaimer, the term of this patent is extended or adjusted under 35 U.S.C. 154(b) by 416 days.

(21) Appl. No.: 14/710,720

(22) Filed: May 13, 2015

(65) Prior Publication Data

US 2015/0327742 A1 Nov. 19, 2015

(30) Foreign Application Priority Data

May 16, 2014 (DE) .................. 10 2014 106 975

(51) Int. Cl.
*A47L 11/40* (2006.01)
*F21V 33/00* (2006.01)
*G01N 21/55* (2014.01)
*A47L 11/282* (2006.01)
*G01J 3/51* (2006.01)
*G01N 21/25* (2006.01)
*F21W 131/30* (2006.01)
*G01N 21/31* (2006.01)

(52) U.S. Cl.
CPC ......... *A47L 11/4011* (2013.01); *A47L 11/282* (2013.01); *A47L 11/4069* (2013.01); *A47L 11/4072* (2013.01); *F21V 33/0044* (2013.01); *G01J 3/51* (2013.01); *G01N 21/251* (2013.01); *G01N 21/255* (2013.01); *G01N 21/55* (2013.01); *A47L 2201/06* (2013.01); *F21W 2131/30* (2013.01); *G01N 2021/3137* (2013.01)

(58) Field of Classification Search
CPC ................ A47L 11/4011; A47L 11/282; A47L 11/4069; A47L 11/4072; F21V 33/0044; G01J 3/51

See application file for complete search history.

(56) References Cited

U.S. PATENT DOCUMENTS 7,599,758 B2 * 10/2009 Reindle ................. A47L 9/2821
15/3
2010/0194288 A1 * 8/2010 Norgaard .................. G01J 1/32
315/149

FOREIGN PATENT DOCUMENTS

DE 102 42 257 A1 4/2003
DE 103 57 637 A1 7/2005

* cited by examiner

*Primary Examiner* — Shay Karls
(74) *Attorney, Agent, or Firm* — Collard & Roe, P.C.

(57) ABSTRACT

A device for cleaning or processing a surface, wherein the device has a light source for illuminating the surface with light and an optical detection device for detecting the light reflected by the surface. In addition, the invention relates to a method for operating a device according to the invention. To create a device for cleaning or processing a surface and a method of the type in question, which differentiates various surfaces with a better resolution than that in the prior art, it is proposed that the optical detection device has at least one filter element and at least one sensor element, which are arranged and designed to detect the light reflected from the surface with respect to at least four different spectral ranges.

12 Claims, 5 Drawing Sheets

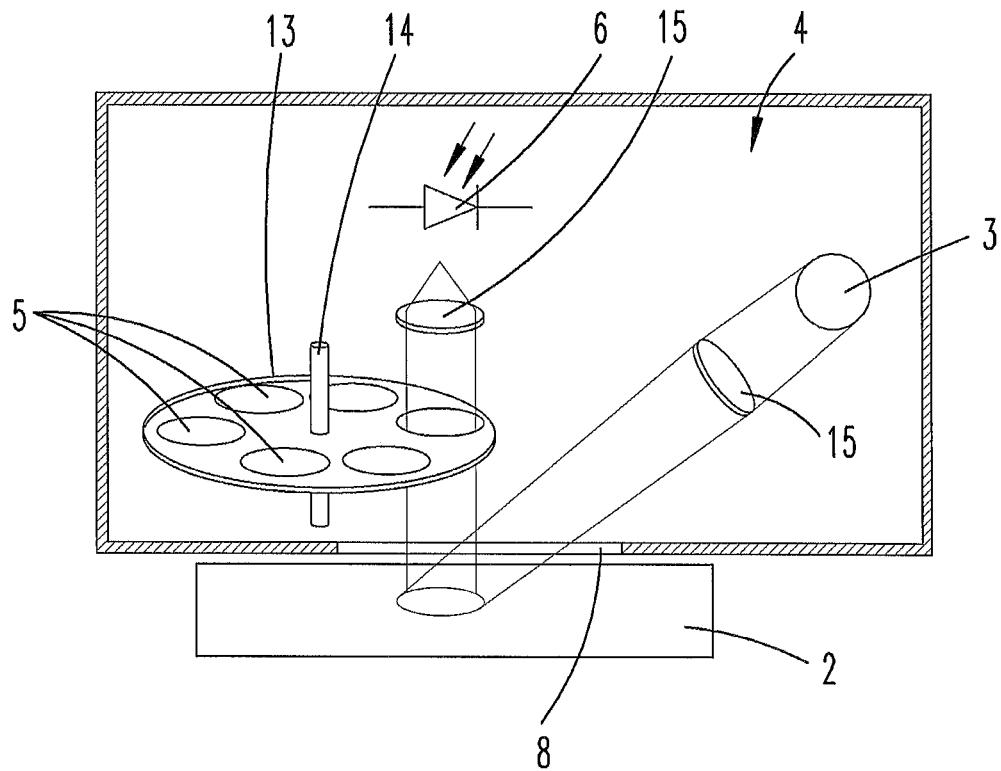
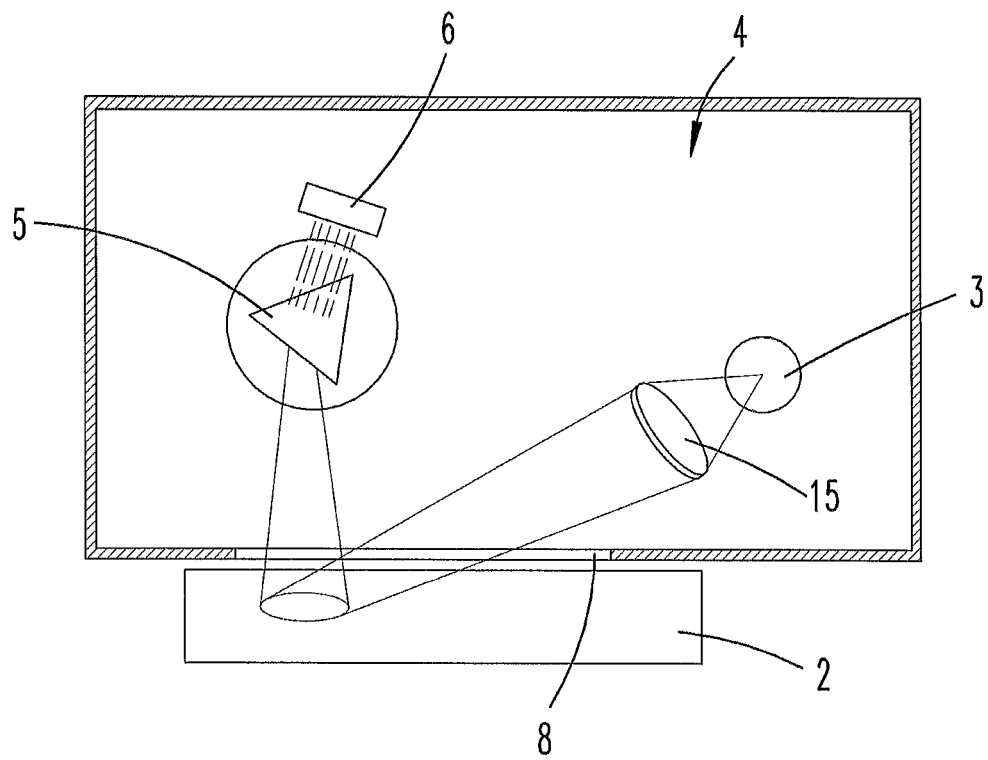

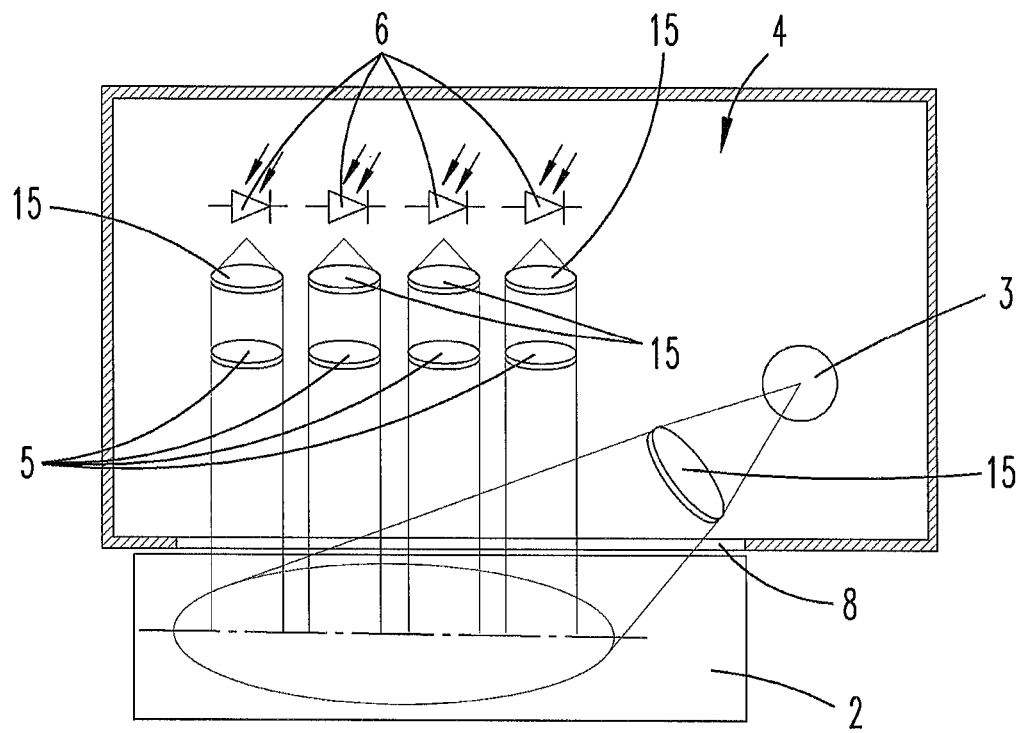

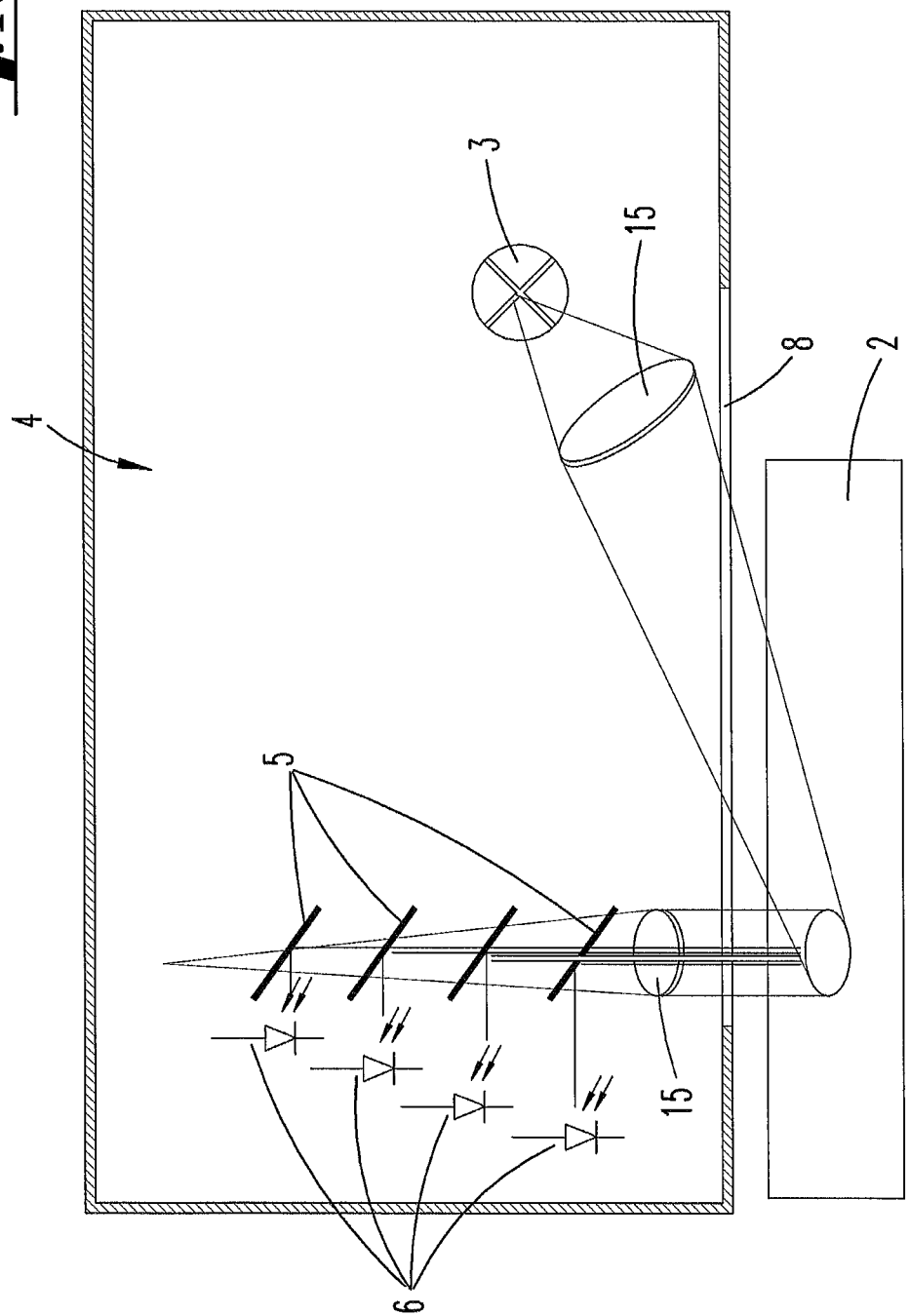

AUTOMATICALLY DRIVEN CLEANING DEVICE

CROSS REFERENCE TO RELATED APPLICATIONS

Applicant claims priority under 35 U.S.C. § 119 of German Application No. 10 2014 106 975.7 filed May 16, 2014, the disclosure of which is incorporated by reference.

BACKGROUND OF THE INVENTION

1. Field of the Invention

The invention relates to a device for cleaning or processing a surface, wherein the device has a light source for illuminating the surface with light and has an optical detection unit for detecting the light reflected from the surface. The device may fundamentally be an automatically driven device or even a handheld device.

In addition, the invention relates to a method for operating a device for cleaning or processing a surface, in which a surface is illuminated with light and the light reflected by the surface is detected.

2. Description of the Related Art

Devices of the aforementioned type are known. They may be, for example, robots for cleaning or care of floor coverings or robots for mowing a lawn. The publication DE 103 57 637 A1 discloses, for example, an automatically driven floor cleaning device, which is suitable for wet cleaning of surfaces, for example, tile floors. DE 102 42 257 A1 describes a vacuum/sweeper robot, for example.

In addition, it is also known in the prior art that such devices can be equipped with cameras, which record photographic images of the surface over which they travel. These photographs are evaluated regularly to detect obstacles or precipices, for example.

In addition, it is also known in the prior art that the photographs taken by the camera can be analyzed to ascertain which type of surface is involved. In practice, cleaning or processing activities should often be limited to certain areas of the floor, for example, individual rooms. In particular, there should be some assurance that a robot for wet cleaning, also known as a mopping robot, will apply water and moisture only to such surfaces that are also suitable for such a cleaning. Therefore, in the prior art, efforts have already been undertaken to design automatically driven, i.e., self-propelled devices, so that the respective surfaces can be analyzed and reliably classified appropriately. On the basis of this classification, the robot can then select suitable movement and cleaning strategies.

Although the devices known in the prior art already have a light source for illumination of the surface with light and an optical detection unit for detection of the light reflected by the surface, these are not sufficient for certain application situations with respect to their spectral resolution. Only three color channels are available for detection, since the optical detection systems of the known devices use a standard color image sensor (RGB sensor). For example, the use of a so-called Bayer sensor, which has a checkerboard type of filter structure, consisting mostly of 50% green filters and 25% each red and blue filter, is especially common. One disadvantage of these sensors is that each color channel supplies only integral color information from a relatively large subsection of the light spectrum. Thus, for example, the green subsection of the light spectrum is not further subdivided into different green hues. Therefore, after detection of light by means of such an RGB sensor, detailed information that would allow conclusions about the original spectral distribution of the radiation reflected at the surface is not available. Accordingly, two green surfaces having different hues of green, for example, could not be differentiated from one another.

Therefore, the object of the present invention is to create a device for cleaning or processing a surface and a method of the type in question, which will differentiate different surfaces with a better resolution in comparison with the state of the art.

SUMMARY OF THE INVENTION

To solve the problem as described above, the present invention proposes a device for cleaning or processing a surface of the aforementioned type, wherein the optical detection unit has at least one filter element and at least one sensor element, which are positioned and designed so that light reflected from the surface is detected with respect to at least four different spectral ranges.

The invention thus creates a device for cleaning or processing a surface, in which a spectral analysis of the light reflected by the surface with a higher resolution than in the state of the art is possible. In comparison with the known devices, which have only optical detection devices with RGB filters, the reflected light can be detected and analyzed with respect to more than three spectral subsections. In this way, for example, different hues of green can also be differentiated. This is valuable in particular wherever surfaces having approximately the same structures but not the same color are encountered. This may be manifested, for example, with similar types of carpet of different colors or similar lawn areas having a different hue of green. It is possible in particular that different cleaning agents must be used on the carpets because of the different colors or that the lawn surfaces are exposed to different amounts of sunlight and should therefore be mowed to a greater or lesser extent.

The optical detection unit may thus be designed in the manner of a multispectral camera, a hyperspectral camera or a microspectrometer.

The detection device may have at least four filter elements for this purpose, wherein each filter element has a spectral range that is different from that of the other filter elements. These filter elements may be arranged on a rotating filter wheel, for example, wherein one of the filter elements is held in the optical axis of the light reflected by the surface for each measurement. Due to the rotation of the filter wheel, thus all the filter elements can be used on the reflected light, one after the other, so that a sensor element arranged in the direction of propagation of the light can measure the differing spectral components of the light, one after the other. Depending on how many filter elements are used with differing spectral ranges, the resolution of the optical detection device can vary. The resolution increases with the number of filter elements used. Fundamentally, especially in those subsections of the light spectrum, an especially large number of filter elements, in which a particularly high resolution is required, may be used. For example, in the case of surfaces which have mainly green hues, an especially large number of filter elements should be provided for the green spectral range, whereas only a few filter elements or none at all need be kept on reserve for the other subsections of spectral ranges.

The filter elements may be band-pass filters or band-stop filters, depending on the type of optical design of the detection device. Band-pass filters select the light in transmission, while band-stop filters select the light in reflection (for example, as dichroic mirrors).

In conjunction with the arrangement of a filter wheel, as presented above, it is advisable for the detection device to have a sensor element assigned jointly to the filter elements. By rotation of the filter wheel equipped with different filter elements, it is possible to bring each of the filter elements in front of the sensor element with respect to the direction of propagation of the reflected light, so that the light is filtered with respect to another spectral range—one after the other chronologically.

The jointly assigned sensor element may especially advantageously be a single photodiode, which is then read out with a repeat rate in time which corresponds to the product of the number of filter elements multiplied times the rotational frequency of the filter wheel—with a uniform circumferential distribution of the filter elements on the filter wheel. Before the optical detection device thus changes from a first filter element to a second filter element, it is advisable to read out the photodiode. Photodiodes are inexpensive, mass-produced products that can be read out without any great equipment expenditure. In addition, photodiodes which have a particularly large pixel area and thus a particularly high sensitivity may also be used. This is advantageous in particular in analysis of surfaces that have only a weak reflective power.

Alternatively, it is also possible for the detection device to have a plurality of sensor elements, wherein a separate sensor element is assigned to each filter element. The sensor elements may be arranged in the manner of a photodiode array, wherein the use of at least four photodiodes is advantageous for the multispectral detection according to the invention. The photodiode array may be an integrated module or may be composed of individual photodiodes, optionally also different types of diodes. A single filter element is assigned to each of the sensor elements, so that the sensor element detects only the light of a certain spectral range. The filter characteristic of the sensor elements may be selected on the whole, so that it covers the entire visible light spectrum. When using four filter elements and four corresponding sensor elements, for example, one red filter and one photodiode may be responsible for detecting the red spectral range, while a yellow filter element and a photodiode are responsible for detecting the yellow light, a green filter element and a photodiode are responsible for detection of the green spectral component, and a blue filter element and a photodiode are responsible for detection of the blue spectral component accordingly.

As an alternative to the aforementioned photodiode array, it is also possible for the detection device to have a CCD chip or a CMOS chip. Different regions of the chip may be illuminated with light of different wavelengths, wherein the data read out of the chip line-by-line, for example, may be assigned to a certain spectral range of the light. According to this embodiment, a plurality of photodiodes is unnecessary.

The invention additionally proposes that the detection device has an optically dispersive element. This yields an alternative to the arrangement of a plurality of filter elements, each of which has a spectral range that is different from that of the other filter elements. In a particularly simple embodiment, the optically dispersive element is a prism or a grating, which splits the light reflected by the surface into its individual spectral components, so that they can strike one or more sensor elements in a spatially separate configuration. It is therefore not necessary to provide a plurality of filter elements. Furthermore, the filter wheel mentioned above, which requires a special mechanism as well as a motor to drive the filter wheel, may also be omitted. To this extent, the optical detection device can be designed to be particularly simple and robust. The optically dispersive element may be used in combination with a plurality of separate sensor elements and also in combination with a CCD chip or a CMOS chip.

The invention also proposes that the wavelength of the light emitted by the light source is coordinated with the reflection properties of at least a portion of the surface. The light source can thus emit in a targeted manner in a spectral range of light for which a portion of the surface has a high degree of reflectivity. A surface can thus be provided with a type of "barrier band," such that this barrier band has a particularly high reflection for a portion of the light spectrum, which is not to be assigned to visible light. For this purpose, the surface can be marked with paint that is invisible to the human eye, for example. Such "invisible paints" are used in marking currency, for example, and can be excited by ultraviolet light, whereupon fluorescent radiation that can be detected by a suitable sensor element is emitted. This yields a special system comprised of a light source, a surface and a sensor element. In addition, such a light source-sensor element system can also be optimized for specific surfaces such as wood, carpet, tile or lawn.

According to the invention, the light source may be a white light source, in particular a halogen lamp or a UV light source. In addition, other light sources which emit in different spectral ranges are also conceivable, depending on the type of surface.

Both the light source and the detection device are advantageously arranged inside a housing of the device, wherein the housing has an outlet opening that is designed and arranged in such a way that the light of the source strikes the surface and the light reflected from the surface strikes the detection device. This arrangement protects the light source and the detection device from soiling, on the one hand, while, on the other hand, it ensures that the light of the light source can emerge from the housing and, after being reflected on the surface, can return back to the housing and be detected there by the detection device.

Finally, the invention provides that the device has an evaluation unit, which is designed to analyze light detected by the detection device with respect to the intensities in the various spectral ranges and to compare them with reference intensities of different surfaces to determine the type of surface. The evaluation unit thus evaluates the light detected by the detection device to ascertain whether and which correspondences there are with known surfaces. If a correspondence is detected, then it can be assumed that the surface being evaluated currently is the known surface. On the basis of this repeat detection, an autonomously functioning device which optimizes its driving strategy and/or cleaning strategy/processing strategy on the detected surface can then be created.

In addition to the device described previously, a method for operating such a device is also created, wherein a surface is illuminated with light, and light reflected by the surface is detected with respect to at least four different spectral ranges.

BRIEF DESCRIPTION OF THE DRAWINGS

The invention is explained in greater detail below on the basis of exemplary embodiments. In the drawings:

FIG. 3 shows a detection device according to a first variant;

FIG. 4 shows a detection device according to a second variant;

FIG. 5 shows a detection device according to a third variant; and

FIG. 6 shows a detection device according to a fourth variant.

DETAILED DESCRIPTION OF THE EMBODIMENTS

Figure 1:
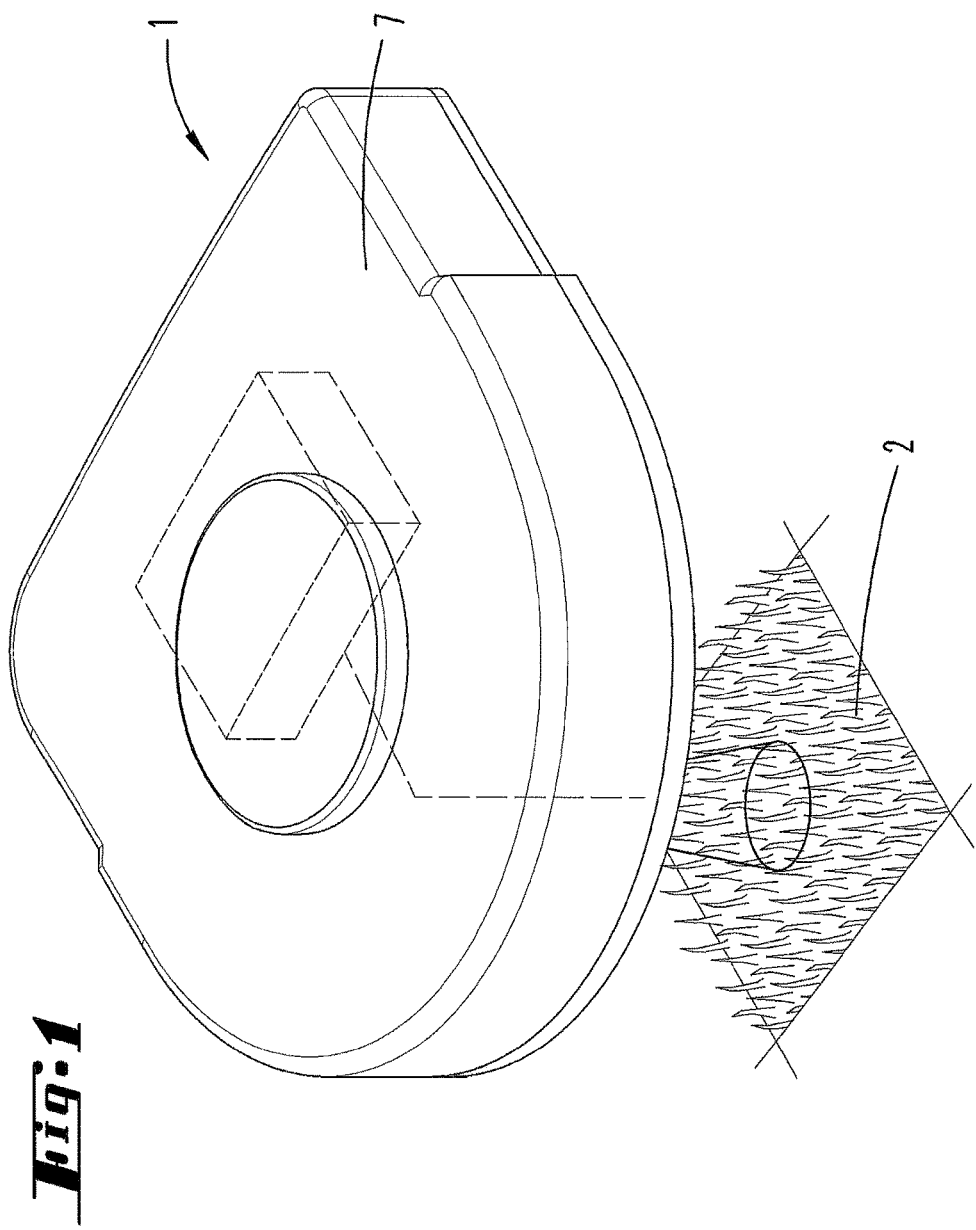
FIG. 1 shows a device according to the invention on a surface.

The device 1 shown in FIG. 1 is a device 1 for cleaning or processing a surface 2. Such devices are used to clean or process surfaces 2. The surfaces 2 may be floor coverings such as carpets, laminate, parquet flooring or something similar as well as optionally lawn areas to be mowed. The device 1, which is shown as an example, is equipped with a controller, which controls the driving and cleaning and/or processing performance of the device 1. Thus, the exemplary device 1 can move around in a room completely independently and can perform cleaning and/or processing operations. A device 1 of this type, which is designed as a vacuum robot, can systematically move through one or more rooms, so that the surface is cleaned completely.

The external appearance of the device 1 is influenced by its housing 7, which may be designed as illustrated in FIG. 1.

Figure 2:
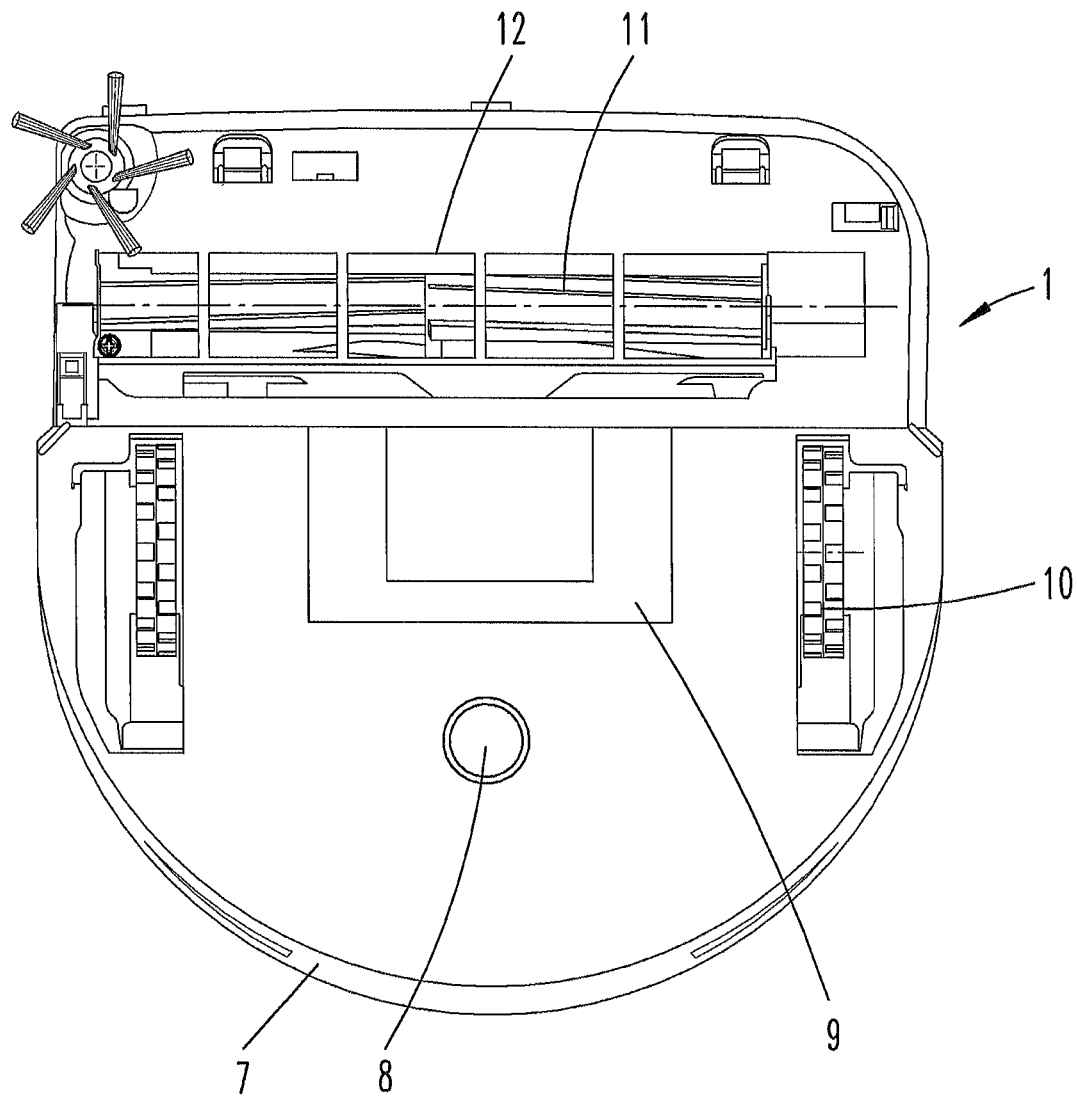
FIG. 2 shows a device according to the invention in a view from beneath.

FIG. 2 shows a device 1 in a view from beneath. The device 1 has, for example, wheels 10, which are driven by an electric motor, as well as a brush 11, which is also driven by an electric motor. The brush 11 is situated inside a vacuum mouth opening 12, which passes through the housing 7, for example, as a totality of window-type openings. To vacuum dust and dirt into a container in the device 1, the device 1 has a suction fan (not shown). In addition, the device 1 has an outlet opening 8 on its bottom inside the housing 7, behind which an optical detection device 4 (not shown in FIG. 2) is provided. Light can be emitted from the housing 7 through this outlet opening 8 and can be directed at the surface 2. An evaluation unit 9, which evaluates the detected signals, is connected to the optical detection device 4.

The power supply to the individual components of the device 1, such as in particular the drive motor for the wheels 10, the electric drive for the brush 11, the motor for the suction fan and additional components, is provided by a rechargeable battery (not shown).

The device 1, shown here as an example, has a controller (not shown), which controls the driving performance and/or cleaning or processing performance of the device 1 as a function of the result of analysis by the evaluation unit 9. The control takes place here as a function of the type of surface 2 detected or parameters such as obstacles arranged on the surface 2 or a degree of soiling of the surface 2. The device 1 may fundamentally be an automatically drivable or even handheld device 1.

As shown in FIGS. 3 to 5, the device 1 has a light source 3 for illumination of the surface 2 with light as well as an optical detection device 4 for detecting the light reflected by the surface 2. In order for the light emitted by the light source 3 arranged inside the housing 7 to be able to reach the surface 2, the housing 7 is provided with an outlet opening 8. Through this outlet opening 8, the light from the light source 3 strikes the surface 2 and is reflected back from the surface 2 at least partially in the direction of the optical detection device 4.

As shown in the figures, the optical detection device 4 has at least one filter element 5 and at least one sensor element 6. The filter element 5 and/or the filter elements 5 and the sensor element 6 and/or the sensor elements 6 are arranged and designed to detect the light reflected from the surface 2 with respect to at least four different spectral ranges.

In the exemplary embodiment according to FIG. 3, the optical detection device 4 has a plurality of filter elements 5 arranged in a filter wheel 13. The total of six filter elements 5 are arranged along a circular path in the filter wheel 13. The filter wheel 13 rotates about an axis of rotation 14, so that the individual filter elements 5 also rotate around the axis of rotation 14 at the same time. A position of the filter elements 5 correlates here with the optical axis of the light reflected by the surface 2. The light reflected by the surface 2 thus passes through the filter elements 5 arranged on the filter wheel 13 in lateral succession. The filter wheel 13 can rotate continuously at a slow speed or the filter wheel 13 can be controlled in such a way that it assumes a targeted position, in which the position of a filter element 5 falls precisely in the optical axis of the reflected light. As soon as this position has been reached, the filter wheel 13 can be stopped to permit a measurement, while the filter elements 5 are stopped. Only when the measurement is concluded can the filter wheel 13 then rotate further until the next filter element 5 reaches the optical axis of the reflected light.

According to FIG. 3, the filter elements 5, which are located inside the filter wheel 13, are designed as transmission filters (band-pass filters). These filters allow precisely the spectral component of light, which corresponds to the filter properties of the filter element 5, to pass through. The filtered component of light then strikes a sensor element 6, which may be a photodiode, for example. It is advisable for a lens 15 to be arranged on the optical axis between the filter element 5 and the sensor element 6 such that this lens focuses the light transmitted by the filter element 5 on the sensor element 6. This lens 15 may be a focusing lens, for example. In addition, it is also possible for the lens 15 to be a lens configuration consisting of a plurality of lenses.

As an alternative to the embodiment of the filter elements 5 as transmission filters (band-pass filters) these filter elements 5 may also be embodied as reflection filters (band-stop filters). In this case, the filter elements 5 would reflect the spectral component of the reflected light to be filtered, so that the sensor element 6 would also be arranged on the side of the filter element 5, which corresponds to the side of the filter element 5 facing the surface 2.

As an alternative to a photodiode, in the case of the sensor element 6 illustrated in FIG. 3, it might also be a conventional camera chip such as a CCD chip or a CMOS chip.

In this exemplary embodiment, the filter wheel 13 is equipped with six different filter elements 5. These filter elements 5 differ with respect to the transmitted spectral ranges of the light. For example, a first filter element 5 may transmit a spectral subsection, while a second filter element 5 transmits a second spectral subsection. For the highest possible resolution of the optical detection device 4, it is advisable for the filter wheel 13 to be occupied by as many different filter elements 5 as possible. The greater the number of filter elements 5 used for detection, the greater the number of spectral subsections, into which the spectrum of the light reflected by the surface 2 can be divided. The sensor element 6, which is a photodiode in this exemplary embodiment, is always read out by the evaluation unit 9, when a new filter element 5 is arranged in the optical axis between the reflecting part of the surface 2 and the photodiode as the sensor element 6. Alternatively, the evaluation unit 9 can also read out the diode current continuously and can use for the analysis the value of the diode current that corresponds to a point in time when the position of a filter element 5 corresponded to the optical axis of the filtered light.

Thus, in a complete 360° rotation of the filter wheel 13, the evaluation unit 9 receives information about the spectral components contained in the light reflected by the surface 2. Since the evaluation unit 9 contains information about the point in time when spectral filter element 5 is in the optical axis of the reflected light, the intensities of the individual spectral light components can be assigned. The evaluation unit 9 creates from this a spectrum of the reflected light and compares this measured spectrum with reference spectra of known surfaces. If a correspondent between the measured spectrum and a reference spectrum is identified, the evaluation unit 9 can recognize the measured surface 2 again. For example, the evaluation unit 9 ascertains that in the case of the surface 2 to be cleaned, this surface is a green carpet. This information can then be used to have the device 1 travel only on an "exposed" surface 2. As soon as the device 1 recognizes that the spectrum of the surface 2 currently being traveled over has changed, a routine can be provided that causes the device 1 to reverse its direction. Likewise, cleaning or processing operations executed by the device 1 can also be controlled as a function of the measured spectrum. For example, different cleaning agents may be used for different colors of the surface 2.

FIG. 4 shows another exemplary embodiment of an optical detection device 4. This optical detection device 4 has a light source 3 as well as a prism as the filter element 5 and a chip as the sensor element 6. The chip may be a CCD chip or a CMOS chip, for example. These chips are usually used in digital cameras. The invention functions according to this embodiment variant in such a way that the light emitted by the light source 3 strikes the surface 2 to be determined and is reflected from there through the outlet opening 8 in the device housing 7 in the direction of the filter element 5. The filter element 5 is, for example, a prism with an equilateral triangle as the base area, which fans out the light reflected by the surface 2 into its spectral components. The spectral components of the light are therefore already separated locally, so that they can be conducted together onto the sensor element 6. The camera chip is then read out line-by-line, for example, so that certain lines can be assigned to defined spectral regions of the reflected light. To this extent, reading out the sensor element 6 yields a spectrum of the reflected light, which reflects the intensities of the individual spectral ranges. As already explained above with respect to FIG. 3, this measured spectrum is then compared with the reference spectra of known surfaces 2, and if a certain surface 2 is recognized, a corresponding traveling routine or cleaning/processing routine of the device 1 is carried out.

As an alternative to the use of the CCD chip or CMOS chip, a photodiode array consisting of photodiodes arranged linearly side-by-side may also be used. In this case, a spectral component of the reflected light is reflected onto a separate photodiode. The spacings of the photodiodes arranged side-by-side are such that the spacing corresponds to the spacing of the spectral components of the light behind the filter element 5, i.e., the prism. By rotating the prism, the distances of the spectral components can also be adapted to a given spacing of the photodiodes.

FIG. 5 shows another exemplary embodiment of an optical detection device 4, which has a certain number of filter elements 5 and a corresponding number of sensor elements 6. The filter elements 5 include, for example, four transmission filters, and the sensor elements 6 include four photodiodes. The photodiodes here are arranged linearly side-by-side, for example, and correspond to the spacings of the filter elements 5 arranged linearly side-by-side. Fundamentally, however, it is also possible to position the filter elements 5 and the sensor elements 6 in a free spatial arrangement. It is important only that they must be situated in the direction of propagation of the light reflected by the surface 2. The light emitted by the light source 3 is widened by means of a lens 15, so that a larger area of the surface 2 is illuminated. The light reflected by the surface 2 strikes the filter elements 5 arranged side-by-side, such that each filter element 5 transmits a certain spectral range of the reflected light. A first filter element 5 can allow a certain green component of the light, for example, to pass through, while a second filter element 5 allows a red component to pass through. The individual spectral components then each reach a separate photodiode via a separate lens system 15. The evaluation unit 9 connected to the photodiodes has information about which photodiode is assigned to which spectral component of the light. Therefore, the evaluation unit 9 can create a spectrum of the light reflected by the surface 2. This measured spectrum is in turn compared with stored spectra of known surfaces 2 and, when recognized, used to control certain operational processes or cleaning/processing operations of the device 1.

FIG. 6 illustrates another exemplary embodiment of an optical detection device 4. This optical detection device 4 also contains filter elements 5 and sensor elements 6 in a corresponding number. In contrast with the arrangement according to FIG. 5, the filter elements 5 are designed as reflection filters. These reflection filters are arranged one after the other in the direction of propagation of the light. A separate sensor element 6 is assigned to each of these filter elements 5. The sensor elements 6 are situated on the side of the filter elements 5 facing the surface 2. Each filter element 5 then reflects a certain spectral range of the light reflected by the surface 2 onto the respective sensor element 6. A first filter element 5 can reflect a certain green component of the light, for example, while a second filter element 5 reflects a red component, and so forth. The spectral components of the light filtered in this way then reach the respective sensor element 6. The further procedure in evaluation of these spectral components with the help of the evaluation unit 9 takes place by analogy with the diagram in FIG. 5, for example.

In all cases, the choice of the light source 3, the filter elements 5 and the sensor elements 6 can be adapted to certain surfaces 2. It is possible, for example, that the surface 2 is equipped with a certain optical property in a targeted manner, so that only certain spectral light components are reflected. In particular the surface 2 may have subsections having markings, which absorb ultraviolet light, for example, and emit fluorescent radiation within a certain spectral range. The fluorescent radiation is excited in a targeted manner by light from a UV light source 3. Both the filter elements 5 and the sensor elements 6 are selected for the corresponding spectral compositions of the emitted fluorescent radiation. Since the expected fluorescent radiation is generally known with respect to its spectral composition, this spectral range may be subjected only to detection, i.e., only filter elements 5 that transmit light of these spectral subsections are used. To this extent, it is possible that red fluorescent light, for example, will be subdivided into additional spectral subsections.

To ensure reliable functioning of the optical detection device 4, it may also be provided within the scope of the invention that reference measurements are performed on a "white standard" at certain intervals in time. Such a "white standard" may be introduced into the interior of the housing 7, for example. Alternatively, for example, it is also possible to perform a reference measurement when the device 1 is situated on a base station. In particular, a baseplate of this base station may then be designed in a "reference color" so that the optical detection device 4 can perform the reference measurement in an unchanged measurement setup and measurement direction. The baseplate of the base station is a surface 2 in the sense of the invention. A reference measurement may be provided, for example, before each detection by the optical detection device 4. Alternatively, however, this may also be repeated after a certain number of measurements or performed regularly once a month or the like.

LIST OF REFERENCE NUMERALS 1 device
2 surface
3 light source
4 detection device
5 filter element
6 sensor element
7 housing
8 outlet opening
9 evaluation unit
10 wheel
11 brush
12 vacuum opening
13 filter wheel
14 axis of rotation
15 lens

What is claimed is:

1. A device for cleaning or processing a surface, comprising:
   a. a light source for illuminating the surface with light, and
   b. an optical detection device for detecting the light reflected by the surface, the optical detection device having at least one optical filter element and at least one sensor element, which are arranged and designed to detect the light reflected from the surface with respect to at least four different spectral ranges, and
   c. an evaluation unit configured for evaluating light detected by the detection device with respect to intensities in different spectral ranges and comparing the intensities with reference intensities of different surfaces in order to determine the type of surface being cleaned or processed.

2. The device according to claim 1, wherein the detection device has at least four filter elements, and wherein each filter element has a spectral range that differs from that of the other filter elements.

3. The device according to claim 2, wherein the detection device has a sensor element assigned jointly to the filter elements.

4. The device according to claim 2, wherein the detection device has a plurality of sensor elements, and wherein a separate sensor element is assigned to each filter element.

5. The device according to claim 1, wherein the sensor element is a photodiode.

6. The device according to claim 1, wherein the sensor element is a CCD chip or a CMOS chip.

7. The device according to claim 1, wherein the filter element is an optically dispersive element.

8. The device according to claim 7, wherein the detection device has a plurality of sensor elements arranged linearly side-by-side.

9. The device according to claim 8, wherein sensor elements are photodiodes.

10. The device according to claim 1, wherein the light source is configured to emit a wavelength of light that is coordinated with reflective properties of at least a portion of the surface.

11. The device according to claim 1, wherein the device further comprises:
    a housing having an outlet opening,
    an electric motor disposed within the housing,
    a brush connected to the electric motor, and
    wheels driven by the electric motor,
    wherein the light source is disposed within the housing and is arranged so that light from the light source is emitted through the outlet opening.

12. A method for operating a device for cleaning or processing a surface, comprising illuminating a surface with light via a light source, and detecting light reflected from the surface with respect to at least four different spectral ranges using an optical detection device having at least one optical filter element and at least one sensor element, and performing a spectral analysis of the light reflected by the surface in order to differentiate different types of surfaces.

* * * * *